United States Patent [19]

Asher et al.

[11] Patent Number: 5,024,213
[45] Date of Patent: Jun. 18, 1991

[54] CONNECTOR FOR A CORRECTIVE DEVICE

[75] Inventors: Marc A. Asher, Prairie Village, Kans.; Walter E. Strippgen, Golden, Colo.; Charles F. Heinig, Charlotte, N.C.; William Carson, Columbia, Mo.

[73] Assignee: AcroMed Corporation, Cleveland, Ohio

[21] Appl. No.: 308,430

[22] Filed: Feb. 8, 1989

[51] Int. Cl.$^5$ .............................................. A61F 5/00
[52] U.S. Cl. ..................................... 128/69; 606/61
[58] Field of Search ........................... 128/69; 606/61; 24/230.5 R, 230.5 AD; 248/316.6

[56] References Cited

U.S. PATENT DOCUMENTS 4,433,676 2/1984 Bobechko ........................... 606/61
4,648,388 3/1987 Steffee ................................ 128/69
4,854,304 8/1989 Zielke ................................. 128/69

FOREIGN PATENT DOCUMENTS 2615095 11/1988 France ................................ 128/69

Primary Examiner—V. Millin
Assistant Examiner—P. Kubel
Attorney, Agent, or Firm—Tarolli, Sundheim & Covell

[57] ABSTRACT

Apparatus for connecting a bendable elongate rod with a vertebra. The apparatus comprises a body portion having an opening for receiving the rod. A connector portion is fixed to and extends from the body portion for connecting the body portion with the vertebra. A pair of spaced apart arcuate surfaces are located in the opening in the body portion for engaging the rod at axially spaced locations.

17 Claims, 4 Drawing Sheets

CONNECTOR FOR A CORRECTIVE DEVICE

BACKGROUND OF THE INVENTION

1. Technical Field

The present invention relates to surgically correcting a deformed and/or degenerated spinal column, and particularly, relates to a connector for attaching a corrective device to a vertebra of a spinal column.

2. Description of the Prior Art

Connectors for attaching corrective devices to vertebrae of a spinal column are known. U.S. Pat. No. 4,648,388 discloses clamps for attaching a bendable rod to vertebrae. One type of clamp includes a clamping portion with an opening for receiving a portion of the rod. The opening has a substantially constant diameter along its longitudinal extent and the diameter of the opening is slightly larger than the outer diameter of the rod. A pair of legs extend from the clamping portion of the clamp and are located adjacent one another. Each of the legs has an opening extending transversely to the opening in the clamping portion. A fastener is received through the openings in the legs to press the legs together and to contract the clamping portion around the rod to grip the rod.

Another type of clamp of U.S. Pat. No. 4,648,388 includes a pair of substantially identical clamp halves. Each clamp half has an arcuate clamping portion with a leg extending therefrom. The arcuate clamping portions of the clamp halves define an opening for receiving the rod. In either type of clamp, once the legs engage, further tightening of the fastener applies very little additional force to the clamping portion to increase the clamping force on the rod.

If a bending moment is applied to the rod which is received in either type of clamp of U.S. Pat. No. 4,648,388, the rod tends to pivot about a point of contact within the clamping portion. If a straight portion of the rod is received in the clamping portion, the rod contacts the clamping portion at diametrically and axially opposite end portions of the clamping portion during the pivoting of the rod. The axial distance between the points of contact of the rod and clamping portion defines a moment arm of a length approximately equal to the longitudinal extent of the clamping portion. A force is applied by the fastener to the legs of the clamp through the moment arm to resist opening of the clamping portion when the rod pivots. If a bent portion of the rod is received in the clamp and contacts the clamp at an end portion and at a point intermediate the axial ends of the clamp, the moment arm is less than the longitudinal extent of the clamp. Thus, a larger force is required to be applied by the fastener to resist opening of the clamping portion due to the same magnitude bending moment in the rod because the force is applied through a shorter moment arm.

SUMMARY OF THE INVENTION

The present invention is directed to an apparatus for connecting a corrective device, such as a bendable elongate rod, to a vertebra of a spinal column. The apparatus comprises a body portion having an opening for receiving a portion of the elongate rod. A connector portion is fixed to and extends from the body portion for connecting the apparatus with the vertebra. A pair of spaced apart arcuate surfaces are located in the opening in the body portion adjacent axial ends of the body portion. The pair of spaced apart arcuate surfaces engage the rod at axially spaced locations.

In one embodiment of the present invention, a hook type connector includes the connector portion having a curved configuration for hooking around a portion of the vertebra. A set screw is threaded into the body portion and is located diametrally opposite the pair of spaced apart arcuate surfaces. The set screw extends into the opening to press the rod against the pair of spaced apart arcuate surfaces.

In another embodiment of the present invention, a split clamp type of connector includes a pair of clamp halves. Each clamp half has an opening for receiving a portion of a fastener for pressing the clamp halves together and for connecting the clamp portions with the vertebra. Each of the clamp halves have an arcuate recess for receiving the rod therebetween. When the clamp halves are pressed together, the rod is securely gripped to restrict relative movement between the rod and the clamp. Axially spaced arcuate surfaces are located in each recess to engage the rod at axially spaced locations when the clamp halves are pressed together by tightening the fastener against the connector portions.

Further improvements to the split clamp type of connector include means for spacing apart end portions of the clamp halves so the arcuate recesses pivot toward one another as the fastener is tightened. The arcuate surfaces engage the rod at spaced locations along the rod to assure the largest possible moment arm for resisting opening of the clamp halves. The axially spaced apart arcuate surfaces are located adjacent an arcuate end of the arcuate recess in each clamp half and a second pair of spaced apart arcuate surfaces are located adjacent another arcuate end of the arcuate recess. The clamping portion is resiliently deflectable and deflects when the clamp halves are pressed around the rod to securely grip the rod.

In yet another embodiment of the present invention, a solid clamp type connector includes a second opening for receiving a fastener to connect the clamp with a vertebra. The second opening extends in a direction transverse to the direction in which the opening for receiving the rod extends. A set screw is threaded into the body portion and presses the rod into engagement with the spaced apart arcuate surfaces.

BRIEF DESCRIPTION OF THE DRAWINGS

Further features of the present invention will become apparent to those skilled in the art to which the present invention relates from reading the following specification with reference to the accompanying drawings, in which.

DESCRIPTION OF PREFERRED EMBODIMENTS

Figure 1:
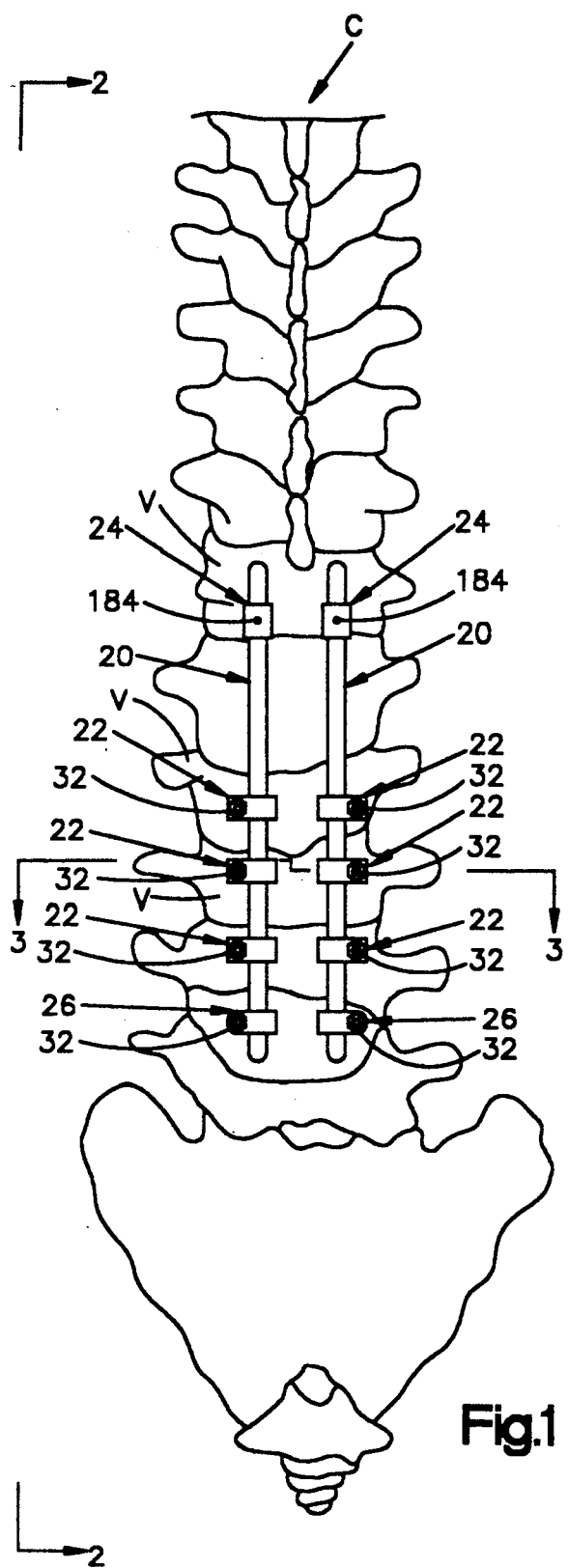
FIG. 1 is a view of a corrective device connected with a portion of a human spinal column by connectors embodying the present invention.
Figure 2:
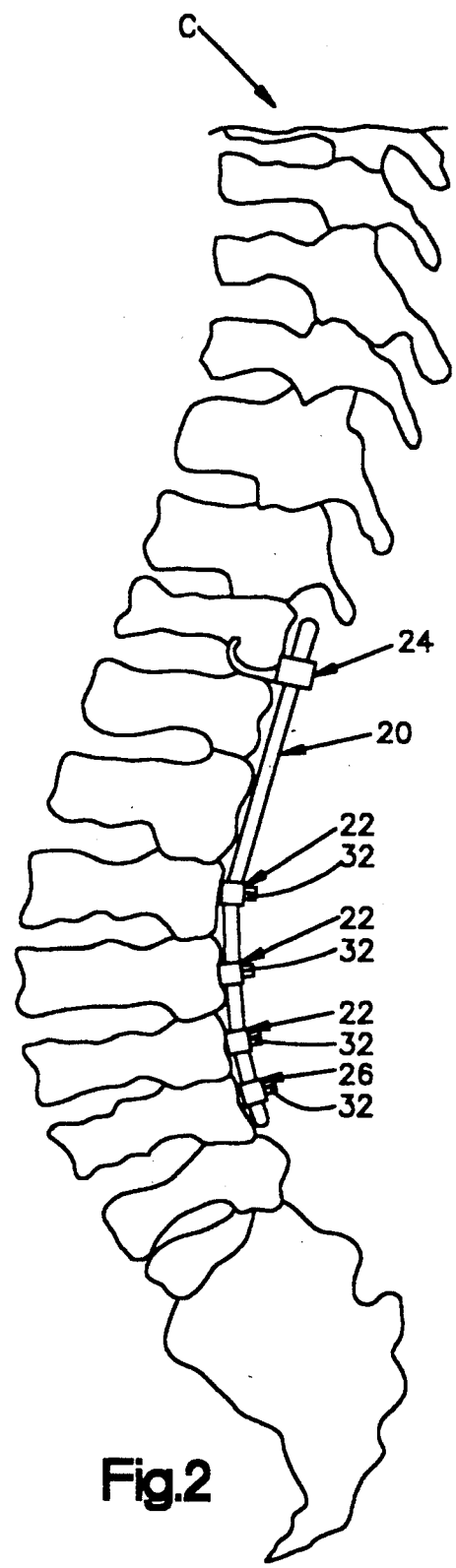
FIG. 2 is a view taken along line 2—2 in FIG. 1.

A pair of surgically implantable rods 20 (FIG. 1) for correcting deformation and/or degeneration of a human spinal column C are connected with several vertebrae V of the spinal column by connectors. The connectors include clamps 22, hooks 24 and clamps 26, all of which embody the present invention. Each rod 20 is elongate and has a circular cross section taken in a plane extending perpendicular to the longitudinal central axis of the rod. The rod 20 is bendable to conform to a desired curvature of the spinal column C, as illustrated in FIG. 2, or in any desired plane. The rod 20 has sufficient strength and rigidity to maintain the vertebrae V in a desired relationship. Several of the vertebra V of the spinal column C are illustrated in FIG. 1 with the spinous processes removed for clarity. Removal of the spinous processes may or may not be necessary during the surgical procedure.

Figure 3:
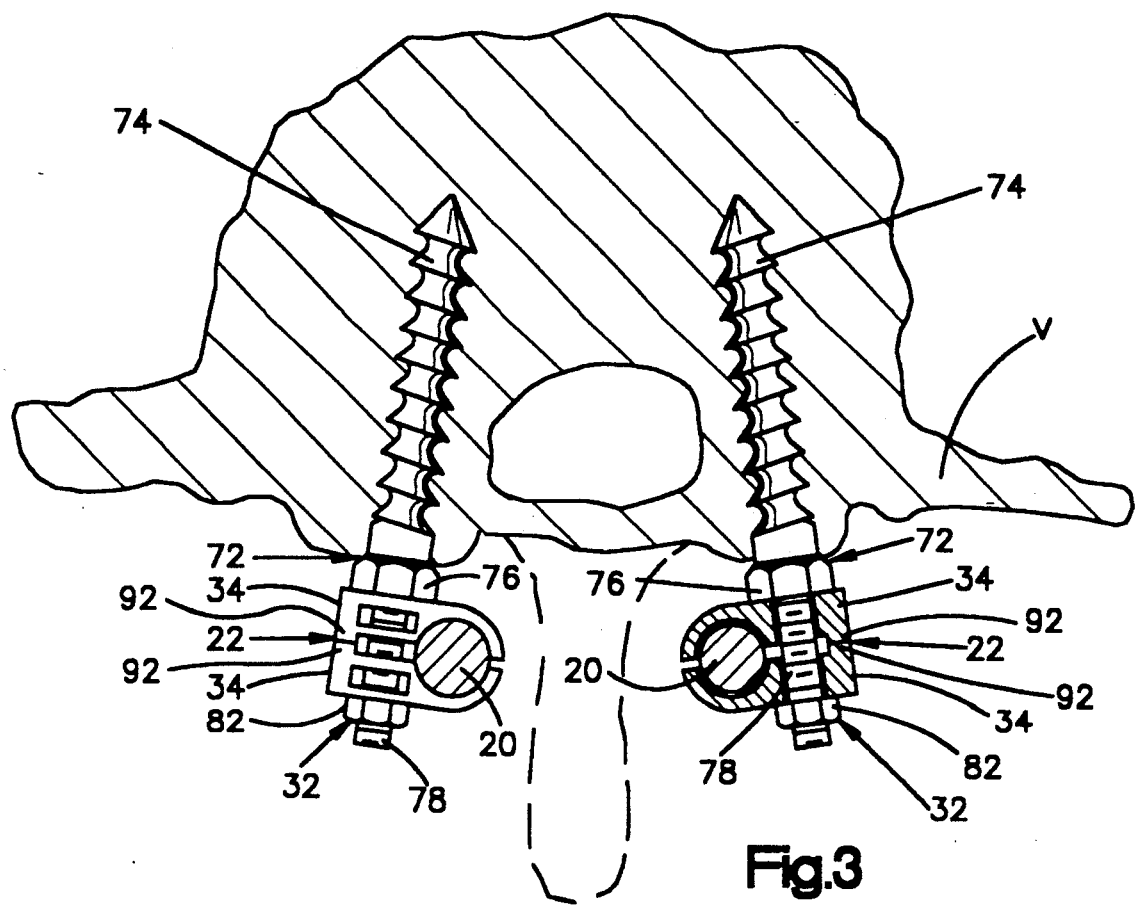
FIG. 3 is a cross sectional view taken approximately along line 3—3 in FIG. 1.

In one embodiment of the present invention, each of the clamps 22 is connected to a respective vertebra V by a fastener 32 (FIG. 3). Each clamp 22 includes a pair of substantially identical clamp halves 34. Each clamp half 34 (FIG. 4) includes a connector portion 42 having an opening 44 for receiving a portion of the fastener 32. A body portion 52 is fixed to and extends from the connector portion 42. The body portion 52 has an arcuate recess 54 for receiving a portion of the rod 20. Recesses 62 are located in opposite sides of the connector portion 42 and receive portions of a tool for holding the clamp half 34 during installation and/or tightening of the fastener 32.

The fastener 32 (FIG. 3) includes a screw 72 having a first threaded end portion 74 for threaded engagement with an opening formed in a pedicle of the vertebra V. The screw 72 has a shoulder portion 76 which establishes how far the first threaded end portion 74 can extend into the vertebra V and spaces the clamp 22 away from engaging the vertebra. The screw 72 has a second threaded end portion 78 extending through the openings 44 in both of the clamp halves 34 of the clamp 22. The fastener 32 also includes a nut 82 threaded onto the second threaded end portion 78 of the screw 72 to press the clamp halves 34 together and against the shoulder 76 of the screw 72.

A spacer portion 92 (FIGS. 4 and 6) is located at an axial end of the connector portion 42 on a side of the opening 44 located opposite the side on which the body portion 52 and recess 54 are located. Upon tightening the nut 82 onto the second threaded end portion 78 of the screw 72, spacer portions 92 on each of the clamp halves 34 make contact with one another, as illustrated in FIG. 3. The spacer portions 92 prevent the connector portions 42 from engaging as the nut 82 is tightened and cause the body portions 52 of the clamp halves 34 to pivot toward one another and align squarely on the rod. The body portions 52 of the clamp halves 34 grip around the rod 20 securely and the force of the nut 82 being tightened is transmitted to press the body portions 52 around the rod 20 instead of being lost by pressing the connector portions 42 of the clamp halves 34 together as may occur if the connector portions engage. A groove 102 is machined in a central portion of the spacer portion 92 to separate the spacer portion into two halves. The groove 102 prevents rocking of the clamp halves 34 about a central portion of the spacer portion 92.

Figure 4:
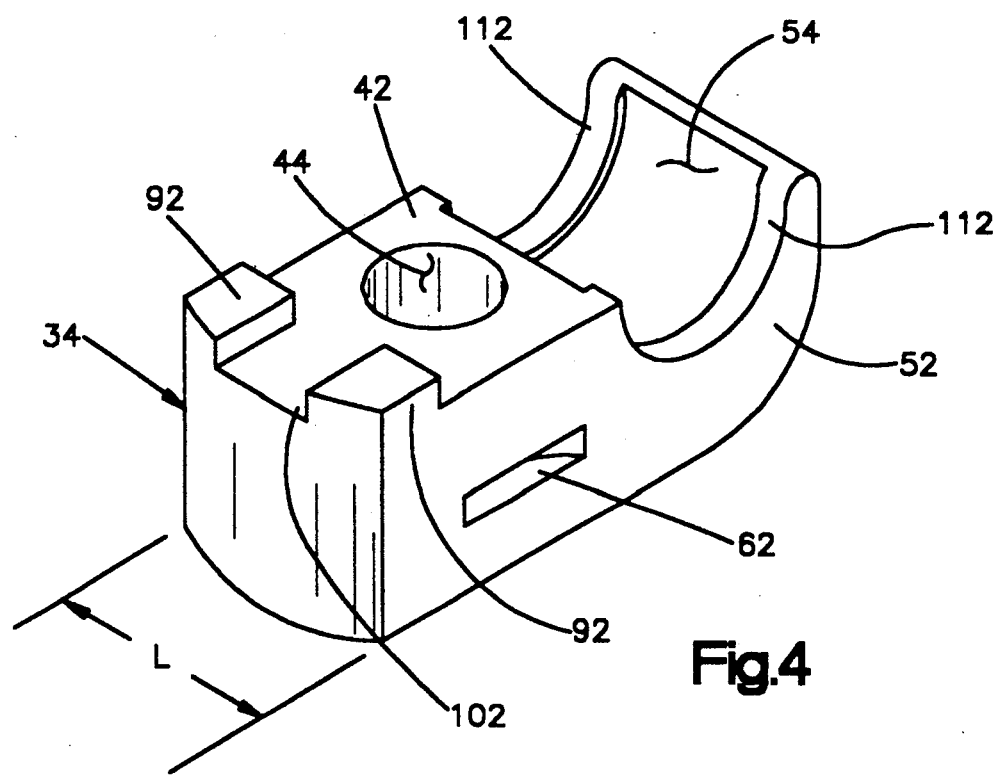
FIG. 4 is an enlarged perspective view of a portion of a clamp illustrated in FIG. 3.

In the embodiment of the clamp half 34, illustrated in FIG. 4, the arcuate recess 54 in the clamp half has a pair of axially spaced apart arcuate surfaces 112 extending radially inwardly from the recess 54. Each arcuate surface 112 engages a portion of the rod 20 at axially spaced locations regardless of whether the rod is straight or bent. Thus, the locations at which the rod 20 engages the clamp halves 34 define a moment arm of approximately the length L of the clamp, when a bending moment is applied to the rod which tends to open the clamp 22. When the bending moment is applied to the rod 20, the forces exerted between the rod 20 and the arcuate surfaces 112 of the clamp 22 are smaller as compared to forces applied over a shorter moment arm that would exist if the rod 20 was not engaged by the clamp halves 34 at axially spaced locations at a length approaching the width L of the clamp.

The body portion 52 is resiliently deflectable. The radius of the arcuate surfaces 112 is slightly less than the radius of the rod 20. When the clamp halves 34 are pressed together, the body portion 52 deflects slightly when the arcuate surfaces 112 engage the rod 20. The radius of the arcuate surfaces 112 increases to equal the radius of the rod 20 so that a gripping force is always applied by the clamp 22 to the rod.

Figure 6:
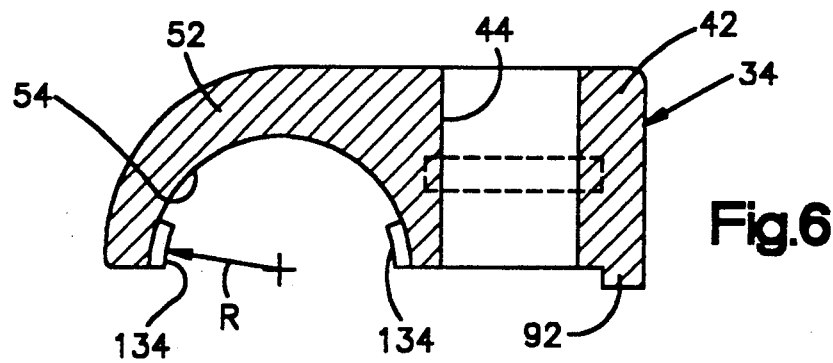
FIG. 6 is a cross sectional view of the portion of the clamp of FIG. 5, taken approximately along line 6—6 in FIG. 5.
Figure 5:
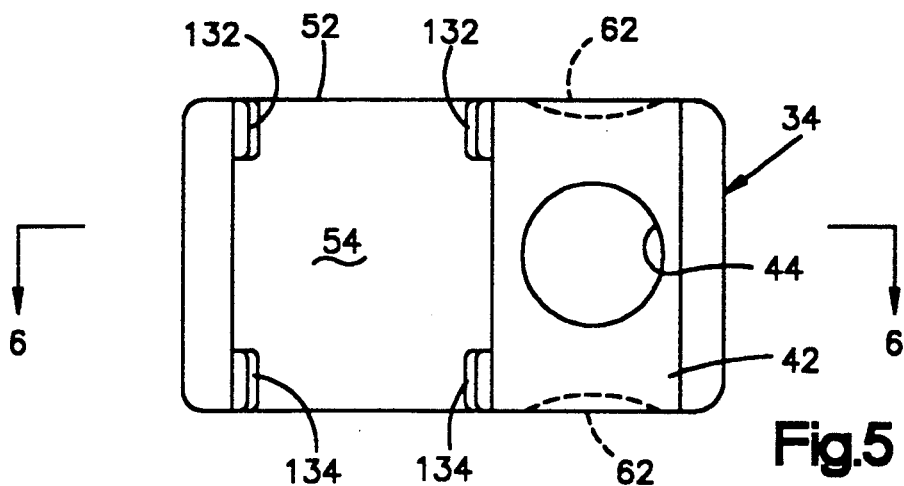
FIG. 5 is a view of a portion of a clamp according to another embodiment of the present invention.

Another embodiment of the clamp half 34 is illustrated in FIGS. 5 and 6. A pair of arcuate surfaces 132, 134 are located at the axial end portions of the recess 54 in the clamp half 34. The arcuate surfaces 132, 134 are located adjacent the arcuate ends of the arcuate recess 54. The radius R of the arcuate surfaces 132, 134 is slightly less than the radius of the rod 20. When the clamp halves 34 are pressed together, the body portion 52 deflects slightly when the arcuate surfaces 132, 134 clamp around the rod 20. The radius R of the arcuate surfaces 132, 134 increases to equal the radius of the rod 20 so that a gripping force is always applied by the clamp 22 to the rod.

Figure 7:
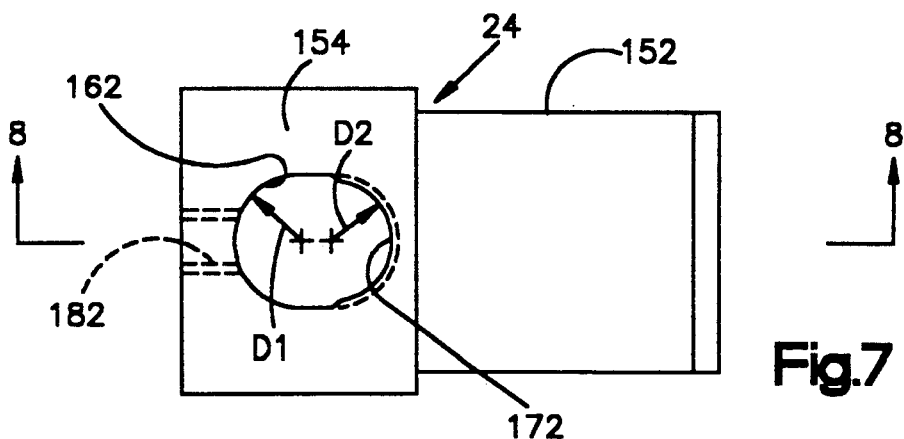
FIG. 7 is an enlarged view of a hook of FIG. 1.
Figure 8:
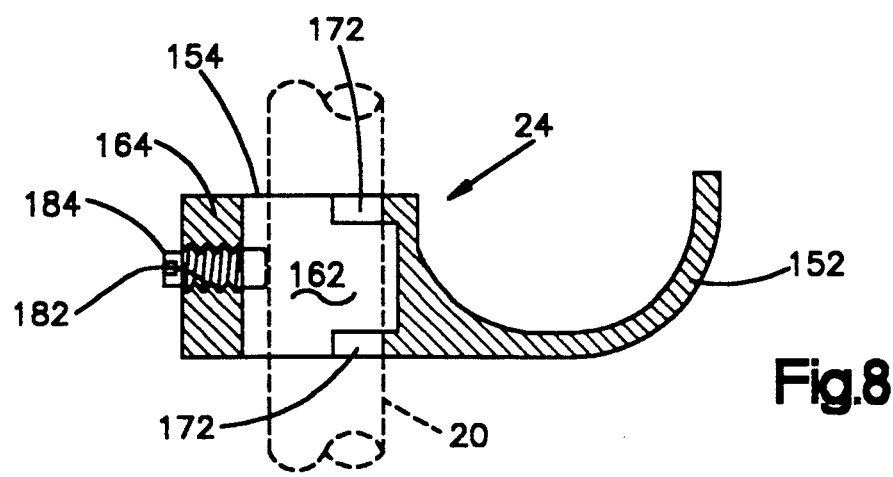
FIG. 8 is a cross sectional view of the hook of FIG. 7, taken approximately along line 8—8 in FIG. 7.

A hook 24 for connecting the rod 20 to a vertebra is illustrated in FIGS. 7 and 8. A curved connector portion 152 of the hook 24 extends around a portion of a vertebra V, as illustrated in FIG. 2, to connect the hook with the vertebra. A body portion 154 of the hook 24 is fixed to the curved connector portion 152. A generally oval-shaped opening 162 (FIG. 7) extends through the body portion 154 of the hook 24 for receiving a portion of the rod 20. The opening 162 has a first larger radius D1 and a second smaller radius D2. The radius D2 defines an axial end of the opening 162 and forms a pair of arcuate surfaces 172. The pair of axially spaced arcuate surfaces 172 shown in FIG. 8, engage portions of the rod 20 at axially spaced locations.

A threaded opening 182 communicates with the opening 162 in the body portion 154 and extends transversely to the longitudinal axis of the opening 162. The opening 162 has a taper 164 extending through the body portion 154 which allows the hook 24 to pivot on the rod 20 to facilitate placement of the connector portion 152 about a portion of vertebra V. A threaded member such as a set screw 184 (FIG. 8) is received in the threaded opening 182. An axial end of the set screw 184 located within the opening 162 engages the rod 20. As the set screw 184 is advanced into the body portion 154, the rod 20 is moved along the opening 162 in the body portion by the set screw and is pressed against the arcuate surfaces 172.

Figure 9:
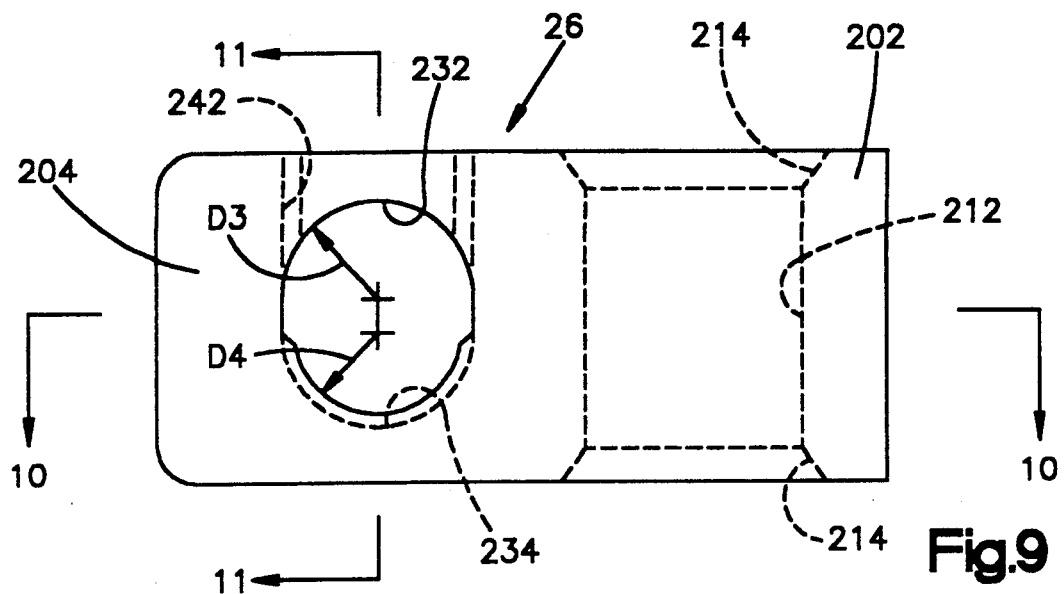
FIG. 9 is a perspective view of a connector according to another embodiment of the present invention.
Figure 10:
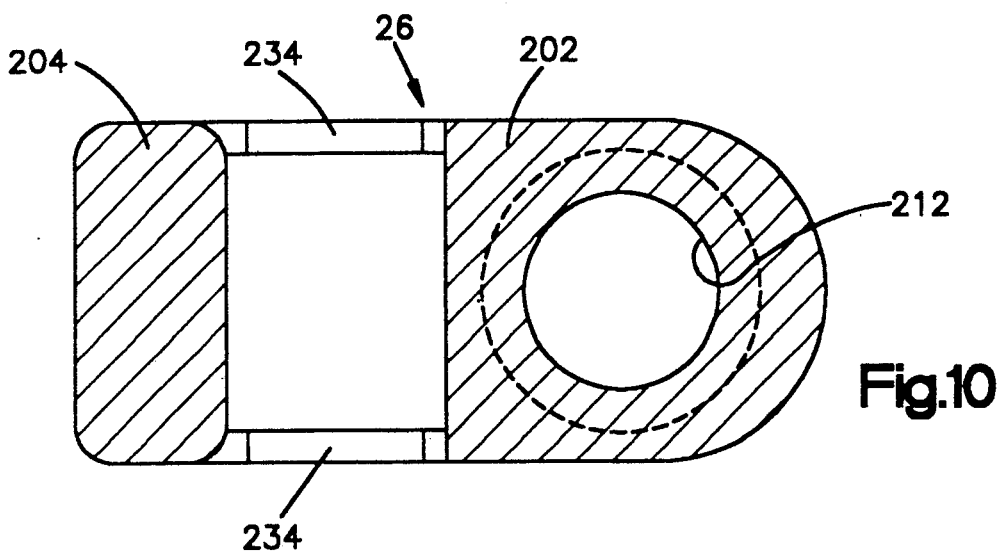
FIG. 10 is a cross sectional view of the connector of FIG. 9, taken approximately along line 10—10 in FIG. 9.
Figure 11:
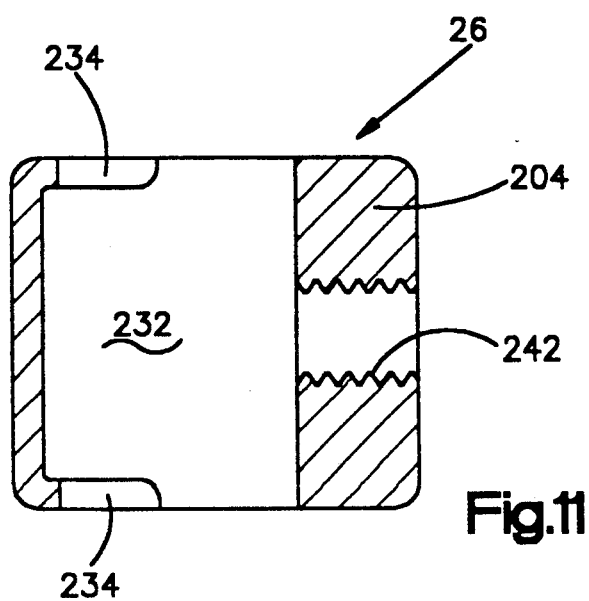
FIG. 11 is a cross sectional view of the connector of FIG. 9, taken approximately along line 11—11 in FIG. 9.

Still another embodiment of the clamp is illustrated as a solid type clamp 26 in FIGS. 9-11 for connecting the rod 20 with a vertebra V. The solid type clamp 26 is preferably machined from a solid piece of metal stock. The solid type clamp 26 includes a connector portion 202 (FIGS. 9 and 10) and a body portion 204. The body portion 204 is integrally formed as one piece with the connector portion 202 during machining of the clamp 26.

An opening 212 extends completely through the connector portion 202. The opening 212 receives a screw of a fastener 32 to connect the clamp 26 to the vertebra V as illustrated in FIG. 1. Axially opposite end portions of the opening 212 have chamfers 214 which together with the opening 212 allow for clearance during installation of the screw of the fastener 32 to the clamp 26.

A generally oval-shaped opening 232 (FIG. 9) extends completely through the body portion 204 of the clamp 26 in a direction generally perpendicular to the opening 212. The opening 232 receives a portion of the rod 20. The opening 232 has a first larger radius D3 and a second smaller radius D4. The radius D3 defines an axial end of the opening 232 and forms a pair of axially spaced apart arcuate surfaces 234 (FIG. 11) for engaging the rod 20 at axially spaced locations, as described above. The body portion 204 also includes a threaded opening 242 for receiving a set screw (not shown) which extends into the opening 232. The set screw is for engaging the rod 20 and pushing the rod 20 against the spaced apart arcuate surfaces 232 when the set screw is advanced in its opening 242. The set screw maintains the rod 20 in engagement with the spaced apart arcuate surfaces 234.

From the above description of preferred embodiments of the invention, those skilled in the art will perceive improvements, changes and modifications. Such improvements, changes and modifications within the skill of the art are intended to be covered by the appended claims.

Having described specific preferred embodiments of the invention, we claim:

1. An apparatus for connecting a bendable elongate rod with a vertebra, said apparatus comprising:
    a body portion including a pair of axially spaced projections located in an opening in said body portion;
    a connector portion fixed to and extending from said body portion for connecting said body portion with the vertebra; and
    said projections of said body portion defining an arcuate recess located between said projections of said body portion, said projections including surfaces for engaging parts of the rod at axially spaced locations when said connector portion acts to connect said body portion with the vertebra.

2. The apparatus set forth in claim 1 wherein said body portion includes a bottom surface further defining the arcuate recess, said surfaces on said projections of said body portion being spaced radially inwardly of the opening from said bottom surface.

3. The apparatus set forth in claim 1 wherein said connector portion includes a curved member for hooking around a portion of the vertebra and further including means for pressing the rod against said surfaces on said projections of said body portion.

4. The apparatus set forth in claim 1 further including surface means defining an opening extending through said connector portion for receiving a fastener to connect said connector portion with the vertebra, the opening in said connector portion extending in a direction transverse to the opening in said body portion, said surfaces on said projections gripping the parts of the rod upon tightening the fastener.

5. The apparatus set forth in claim 1 further including means for pressing the rod against said surfaces on said projections of said body portion.

6. A clamp for clamping a portion of an elongate bendable rod having a circular cross section taken in a plane extending perpendicular to the longitudinal central axis of the rod and for connecting the rod with a vertebra, said clamp comprising:
    a first clamp half including a first body portion having a pair of spaced projections located in an opening in said first body portion;
    a second clamp half including a second body portion having a pair of spaced projections located in an opening in said second body portion;
    said projections of said first body portion defining an arcuate recess located between said projections of said first body portion, said projections of said first body portion including surfaces for engaging parts of the rod at axially spaced locations; and
    means for pressing said connector portions together to clamp the rod in said first and second body portions of said first and second clamp halves.

7. The clamp set forth in claim 6 wherein each of said surfaces is arcuate and has a radius less than the radius of the rod and wherein said first body portion is resiliently deflectable so that the radius of each of said surfaces increases to equal the radius of the rod upon said connector portions being pressed together to securely grip the rod.

8. The clamp set forth in claim 7 wherein said projections of said second body portion define an arcuate recess located between said projections of said second body portion, said projections of said second body portion including surfaces for engaging parts of the rod at axially spaced locations, said surfaces on said projections of said body portions being located at a first arcuate end portion of the openings in said body portions in each of said first and second clamp halves.

9. The clamp set forth in claim 8 wherein said projections of said first body portion include other surfaces for engaging parts of the rod at other axially spaced locations and said projections of said second body portion include other surfaces for engaging parts of the rod at other axially spaced locations, said other surfaces on said projections of said body portions being located at a second arcuate end portion of the openings in said body portions in each of said first and second clamp halves, said second arcuate end portion being located opposite said first arcuate end portion.

10. An apparatus for connecting a bendable elongate rod with a vertebra, said apparatus comprising:
    a body portion including a pair of axially spaced projections located in an opening in said body portion;

a curved portion fixed to and extending from said body portion for hooking around a portion of the vertebra to connect said body portion with the vertebra; and said projections of said body portion defining an arcuate recess located between said projections of said body portion, said projections including surfaces for engaging parts of the rod at axially spaced locations when said curved portion acts to connect said body portion with the vertebra.

11. The apparatus set forth in claim 10 further including means for pressing the rod against said surfaces on said projections of said body portion to clamp the rod.

12. A clamp for clamping a portion of an elongate bendable rod having a circular cross section taken in a plane extending perpendicular to the longitudinal central axis of the rod and for connecting the rod with a vertebra, said clamp comprising:

a first clamp half including a first body portion having a recess for receiving the rod and a connector portion fixed to and extending from said first body portion;

a second clamp half including a second body portion having a recess for receiving the rod and a connector portion fixed to and extending from said second body portion;

a pair of spaced apart arcuate surfaces located in the recesses of said first and second body portions for engaging the rod at axially spaced locations;

means for pressing said connector portions together to clamp the rod in said first and second body portions; and means for spacing apart said connector portions of said clamp halves and for allowing pivoting of said first and second body portions toward one another as said connector portions of said clamp halves are pressed together, said spacing means comprising a projection extending from said connector portion of said first clamp half for engaging said connector portion of said second clamp half at a location on a side of said pressing means opposite said first and second body portions.

13. A clamp for connecting a member with a vertebra, said clamp comprising:

a first clamp half including a first body portion and a first connector portion fixed to and extending from said first body portion and having a first end portion located distal said first body portion;

a second clamp half including a second body portion having a recess for receiving a portion of the member and a second connector portion fixed to and extending from said second body portion and having a second end portion;

means for pressing said connector portions together to clamp the member in said body portions; and means located between said end portions for spacing said connector portions apart and for enabling pivoting of said body portions relatively toward one another about said end portions as said connector portions are pressed together.

14. A clamp for connecting a member with a vertebra, said clamp comprising:

a first clamp half including a first body portion and a first connector portion fixed to and extending from said first body portion and having a first end portion located distal said first body portion;

a second clamp half including a second body portion having a recess for receiving a portion of the member and a second connector portion fixed to and extending from said second body portion and having a second end portion;

means for pressing said connector portions together to clamp the member in said body portions;

means located between said end portions for spacing said connector portions apart and for enabling pivoting of said body portions relatively toward one another about said end portions as said connector portions are pressed together; and a pair of spaced apart arcuate surfaces located in the recesses of said body portions for engaging the member at axially spaced locations.

15. A clamp for connecting a member with a vertebra, said clamp comprising:

a first clamp half including a first body portion and a first connector portion fixed to and extending from said first body portion and having a first end portion located distal said first body portion;

a second clamp half including a second body portion having a recess for receiving a portion of the member and a second connector portion fixed to and extending from said second body portion and having a second end portion;

means for pressing said connector portions together to clamp the member in said body portions;

means located between said end portions for spacing said connector portions apart and for enabling pivoting of said body portions relatively toward one another about said end portions as said connector portions are pressed together; and said spacing means comprises a projection extending from said end portion of said connector portion of at least one of said first and second clamp halves.

16. A clamp for gripping an elongate bendable rod having circular cross section taken in a plane extending perpendicular to the longitudinal central axis of the rod and for connecting the rod to a vertebra, said clamp comprising:

a body portion;

a connecting portion fixed to and extending from said body portion for connecting said body portion with the vertebra;

surface means defining an arcuate recess in said body portion;

a first projection defining the recess and being located at a first end portion of the recess and for engaging a portion of the rod; and a second projection defining the recess and being located at a second arcuate end portion of the recess and for engaging another portion of the rod and being intersected by a plane extending substantially perpendicular to the longitudinal central axis of the rod and intersecting said first projection.

17. The clamp set forth in claim 16 wherein each of said projections has an arcuate surface of a radius less than the radius of the rod and wherein said body portion is resiliently deflectable so that said first and second projections securely grip the rod when said body portion is pressed against the rod.

* * * * *